(12) United States Patent
Boverie

(10) Patent No.: US 7,609,168 B2
(45) Date of Patent: Oct. 27, 2009

(54) METHOD FOR DETECTING CHARACTERISTIC MOVEMENTS OF A VEHICLE DRIVER FOR THE PURPOSE OF DIAGNOSING A LOWERING OF VIGILANCE BY SAID DRIVER

(75) Inventor: Serge Boverie, Plaisance du Touch (FR)

(73) Assignee: Continental Automotive France, Toulouse (FR)

( * ) Notice: Subject to any disclaimer, the term of this patent is extended or adjusted under 35 U.S.C. 154(b) by 337 days.

(21) Appl. No.: 11/641,013

(22) Filed: Dec. 19, 2006

(65) Prior Publication Data

US 2007/0146131 A1 Jun. 28, 2007

(30) Foreign Application Priority Data

Dec. 23, 2005 (FR) .................................. 05 13249

(51) Int. Cl.
*G08B 25/00* (2006.01)
(52) U.S. Cl. ..................... 340/576; 340/573.1; 340/575; 340/665; 340/667; 73/781; 180/273
(58) Field of Classification Search ................ 340/576, 340/573.1, 575, 439, 665, 666, 667, 686.1; 73/65.01, 65.09, 781, 535; 180/272, 273; 701/45
See application file for complete search history.

(56) References Cited

U.S. PATENT DOCUMENTS

| 6,158,768 A | * | 12/2000 | Steffens et al. | 280/735 |
| 6,392,550 B1 | * | 5/2002 | Najor | 340/576 |
| 6,609,054 B2 | * | 8/2003 | Wallace | 701/45 |
| 2006/0283652 A1 | * | 12/2006 | Yanai et al. | 180/272 |

FOREIGN PATENT DOCUMENTS

EP 1475274 11/2004

* cited by examiner

*Primary Examiner*—Toan N Pham
(74) *Attorney, Agent, or Firm*—Young & Thompson (57) ABSTRACT

A method for detecting characteristic movements of a vehicle driver for diagnosing a lowering of vigilance by the driver. In a preliminary phase, the surface of the seat base and of the backrest of the seat is divided into a plurality of elementary surfaces in each of which is embedded a pressure sensor able to detect the pressings and releasings applied by the driver on the pressure sensor, and a plurality of specific movements is selected, each of which includes the determination of at least one geographic zone subjected to a "pressing" or a "releasing" resulting from the movement. The data processing includes analyzing the measurement signals provided by the pressure sensors and comparing, at each sampling time, the possible detected geographic zones of pressing and releasing with each stored geographic zone, in order to provide information on detection of a specific movement when there is a correlation between the geographic zones.

10 Claims, 4 Drawing Sheets

METHOD FOR DETECTING CHARACTERISTIC MOVEMENTS OF A VEHICLE DRIVER FOR THE PURPOSE OF DIAGNOSING A LOWERING OF VIGILANCE BY SAID DRIVER

The invention relates to a method for detecting characteristic movements of a vehicle driver for the purpose of diagnosing a lowering of vigilance by said driver.

Among the data representing the evolution of the lowering of vigilance by a driver, it has been established that certain body movements of drivers can constitute a good indicator for the purpose of diagnosing a lowering of vigilance.

On the basis of this principle, the essential purpose of the invention is to provide a method making it possible to detect, in a systematic and reliable manner, predetermined specific movements of the body of a driver.

For this purpose, and firstly, the invention relates to a method for detecting characteristic movements of a vehicle driver in the driving position on a seat comprising a seat base and a backrest, said detection method consisting in:

dividing the surface of the seat base and of the backrest of the seat into a plurality of elementary surfaces in each of which is embedded a pressure sensor able to detect:

an increase in the pressure applied on the elementary surface, representing a positive pressure, called "pressing" applied by the driver on the pressure sensor, a reduction of the pressure applied on the elementary surface, representing a reduction or a cancellation, called "releasing", of the pressure applied by the driver on the pressure sensor, selecting a plurality of specific movements, such as the movements of the top of the body, repositioning on the seat base (A), transverse rocking toward a driving position offset to one side, longitudinal rocking toward a pushed-in driving position in the top of the backrest (D), and in characterizing each of said specific movements by the determination of at least one geographic zone subjected to a "pressing" or a "releasing" resulting from said movement, and analyzing, with a given sampling period, the measurement signals provided by the pressure sensors, and in comparing, at each sampling time t, the possible geographic zones of pressing or releasing detected with each of the predetermined geographic zones, in such a way as to provide information on detecting a specific movement during a correlation between said geographic zones.

Advantageously, according to the invention, the characteristic geographic zones of the specific movements correspond to zones enveloping contact surfaces of various parts of the driver's body with the seat base and the backrest: complete back, parts of the back (left, right, top, bottom), complete posterior or bottom or top part of the posterior, posterior or parts of posterior (right or left), left or right leg, etc.

Moreover, this method advantageously consists, for the purpose of characterization of given specific movements, in determining at least one geographic zone subjected to a "pressing" or a "releasing", and a time sequence of stressing said geographic zone consisting of an alternation of a period of activation, by pressing or releasing, and a period of non-activation.

A method such as defined above generally makes it possible to detect various types of movement and in particular four advantageous specific movements as described below.

The first of these movements consists in a movement of the top of the back, and for the purpose of its advantageous detection according to the invention:

for the purpose of characterizing said movement, the following are determined:

at least one geographic zone subjected to a "pressing", corresponding to a zone enveloping contact surfaces between the central portion of a driver's back and the backrest and at least one geographic zone subjected to a "releasing", corresponding to a zone enveloping contact surfaces between a driver's posterior and the seat base, and information on the detection of a movement of the top of the back is provided uniquely when there is correlation of a detected geographic zone with:

a said geographic zone of the backrest, and/or a said geographic zone of the seat base, provided that there is, in addition, a minimal degree of symmetry, with respect to a longitudinal axis of the seat base, of the elementary surfaces constituting said detected geographic zone.

The second movement consists in a repositioning movement, and for the purpose of its advantageous detection according to the invention:

two geographic zones subjected to a "releasing" are determined, each one corresponding with a zone enveloping the contact surface between a leg of the driver and the seat base, and information on the detection of a repositioning movement is provided uniquely at the time of detection of the following time sequence:

at a time t: correlation of a detected geographic zone with one of said geographic zones of the seat base, and at a time t+1: absence of activation of the correlated geographic zone at time t, combined with a correlation of a detected geographic zone with the other geographic zone of the seat base.

Two other procedures can also be used according to the invention for detecting a repositioning movement.

According to the first of these two procedures, and advantageously according to the invention:

for the purpose of characterizing the movement, the following are determined:

two geographic zones subjected to a "pressing", corresponding to the two respective zones enveloping contact surfaces between the right and left parts of the bottom of a driver's back and the backrest, and two geographic zones subjected to a "releasing", corresponding with the two respective zones enveloping contact surfaces between the left and right parts of a driver's posterior and the seat base, and information on the detection of a repositioning movement is provided when there is, simultaneously:

correlation of a detected geographic zone with a said right (or left) geographic zone of the backrest, combined with the absence of activation of the other said geographic zone of the backrest, correlation of a detected geographic zone with said left (or right) geographic zone of the seat base, combined with the absence of activation of the other said geographic zone of the seat base.

According to the second procedure, and advantageously according to the invention:

for the purpose of characterizing the repositioning movement, the following are determined:

a geographic zone subjected to a "pressing", corresponding to the zone enveloping the contact surface between the complete back of a driver and the backrest, and a geographic zone subjected to a "releasing", corresponding to the zone enveloping the contact surface between the complete posterior of a driver and the seat base, and information on the detection of a repositioning movement is provided when there is correlation between a detected geographic zone and said geographic zone of the backrest and/or said geographic zone of the seat base.

The third specific movement to which the invention relates consists in a movement of transition toward an offset driving position and, for the purpose of its advantageous detection according to the invention:

for the purpose of characterizing said movement, the following are determined:
two geographic zones subjected to a "pressing", corresponding to two respective zones enveloping contact surfaces between the right and left parts of a driver's back and the backrest,
and two geographic zones subjected to a "releasing" each corresponding to a zone enveloping the contact surface between a leg of the driver and the seat base, and information on the detection of a transition movement is provided uniquely at the time of detection of the following time sequence:
at a time t: correlation of a detected geographic zone with one of said geographic zones of the seat base, and absence of activation of the geographic zone of the backrest symmetrical with said detected zone of the seat base,
at a time t+1: absence of activation of the correlated geographic zone of the seat base at time t, combined with a correlation of a detected geographic zone with the other geographic zone of the seat base.

The fourth specific movement to which the invention relates consists, finally, in a movement of transition toward a "pushed-in" driving position in the top of the backrest. For the purpose of detecting this movement and in an advantageous manner according to the invention:

for the purpose of characterizing said movement, the following are determined:
two geographic zones subjected to a "pressing", corresponding to two respective zones enveloping contact surfaces between the top and bottom parts of a driver's back and the backrest,
and two geographic zones subjected to a "releasing", corresponding with two respective zones enveloping contact surfaces between the top and bottom parts of a driver's posterior and the seat base, and information on the detection of a transition movement is provided at the time, on the one hand, of simultaneous correlation of two detected geographic zones with, respectively, said geographic zones corresponding to the top parts of the back and of the posterior and, on the other hand, the combined absence of activation of said geographic zones corresponding with the bottom parts of the back and of the posterior.

Moreover, according to the invention, advantageous use is made of pressure sensors consisting of differential pressure sensors able to measure the dynamics of the force applied to the corresponding elementary surface.

Moreover, at the time of implementation of the method according to the invention, and during a preliminary phase following the starting of the vehicle, called a thresholding phase, there is advantageously carried out a processing of the signals provided by the pressure sensors, consisting in calculating, for each of said sensors, the respective means of the largest positive and negative variations of the values of said signals, in order to determine respectively negative and positive threshold values for the subsequent extraction of signals representing a pressing or a releasing.

Such a thresholding phase makes it possible to adapt the thresholds subsequently used for the extraction of "useful" signals according to the behavior of each driver.

In order to do this, these variable thresholds are, furthermore, calculated during the first minutes of driving, that is to say during a period when, normally, the driver is not in a state of hypovigilance and when he is driving in a stable manner.

Moreover, for the purpose of refining and completing the transmitted information:
each activated elementary surface of a geographic zone is allocated a weight weighted by the use of a mathematical method such as fuzzy logic, as a function of:
the geographic position, in particular positioning in a bordering zone, of said elementary surface within the geographic zone,
and/or the amplitude of the signal provided by the associated pressure sensor, representative of the level of activation of said elementary surface,
and, for each geographic zone, the following are determined a degree of activation of the latter calculated from the weight of each of the elementary surfaces, in such a way as to associate with each item of information of detection of a specific movement, information representing the degree of belonging to this category of movement.

Other features, objectives and advantages of the invention will emerge from the following detailed description given with reference to the appended drawings which show a preferred embodiment of it as a non-limiting example:

The method according to the invention described below with reference to the appended drawings consists in a method of detecting four different categories of specific movements made by a vehicle driver in the driving position on a seat S comprising a seat base A and a backrest D. More specifically, the purpose of this detection method is to make it possible to diagnose a lowering of vigilance by said driver.

Figure 1:
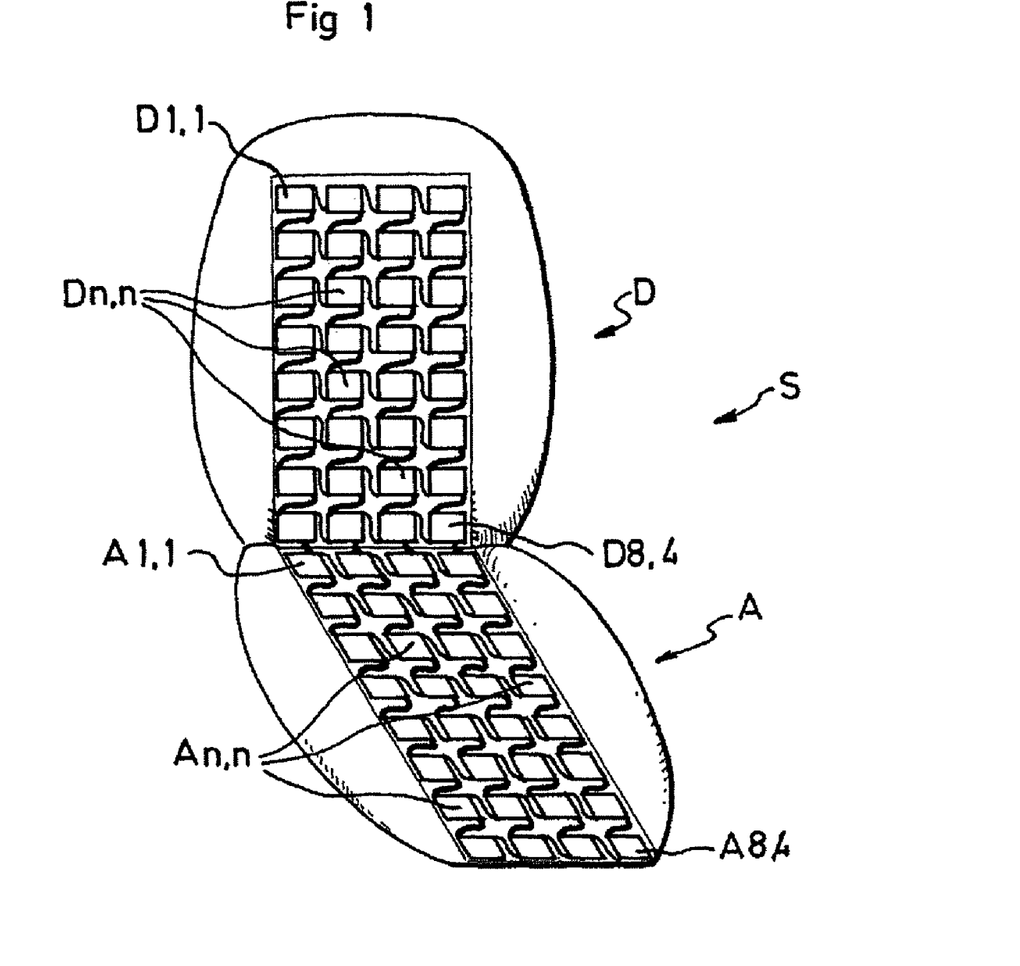
FIG. 1 is a diagrammatic perspective view of a motor vehicle seat intended for the implementation of the detection method according to the invention.

As shown in FIG. 1, for the purpose of implementing this detection method, the seat base A and the backrest D of the seat S are each covered with a sheet of flexible pressure sensors, An,n and Dn,n respectively, each one delimiting an elementary seat base or backrest surface.

In this example, each sheet of sensors is constituted by a matrix of thirty two sensors distributed in eight lines and four orthogonal columns, that is to say, respectively:

32 sensors A1,1 to A8,4 distributed over the seat base A in such a way as to provide signals representing the movements of the bottom of the body, and 32 sensors D1,1 to D8,4 distributed over the backrest D in such a way as to provide signals representing the movements of the top of the body.

Figure 2:
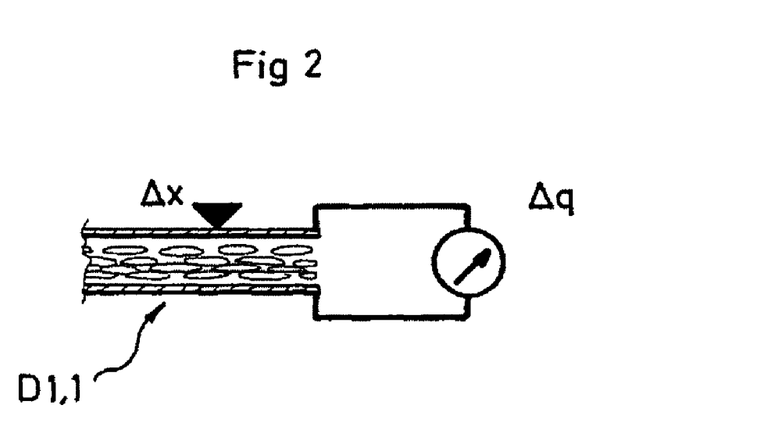
FIG. 2 is a diagrammatic view showing the pressure sensor type and principle used according to the invention.

Moreover, as shown in FIG. 2, each pressure sensor such as D1,1 is of the type constituted from a porous insulating material composed of thin layers of polymers separated by air pockets.

Such a material has the feature of containing microscopic electrical charges and of having a behavior similar to that of piezoelectric materials.

As shown in FIG. 2, this behavior of the piezoelectric type results in the generation of an electrical charge $\Delta q$ when there is application of a force $\Delta x$ tending to vary the thickness of the porous material constituting the pressure sensor.

Therefore, a pressing force applied on a pressure sensor results in a positive peak in the signal provided by said pressure sensor, corresponding to the compression of the porous material, whilst a negative peak is generated when the pressure is released.

Consequently, such pressure sensors have the advantage of being able to detect variations of pressing because they measure the dynamics of the applied force.

According to the invention, the processing of the signal provided by each pressure sensor consists, firstly, in filtering that signal in such a way as to eliminate the interference noises generated by the road, the vibrations of the automobile, etc., which are situated in the top part of the frequency spectrum of the signal.

For this purpose, this filtering is carried out by an "averager".

The second processing operation of the signals provided by the pressure sensors consists in a thresholding operation used solely during a preliminary phase following the starting of the vehicle, called a thresholding phase, during which a processing of the signals is carried out consisting in calculating, for each of said sensors, the respective means of the largest positive and negative variations of the values of said signals in order to determine respectively positive and negative threshold values for the subsequent extraction of the signals.

Firstly, this processing is implemented each time the vehicle is started, during the first minutes following this starting, such that the thresholds are adapted to the driving characteristics of the driver present in the vehicle.

Moreover, this processing results in the calculating of a positive threshold and of a negative threshold, in such a way as to take account of the slightly asymmetrical behavior of the pressure sensors, and to compensate for the differences in dynamics resulting from this asymmetrical behavior.

Finally, this processing is also applied separately to the sensors An,n respectively, integrated in the seat base A and to the sensors Dn,n integrated in the backrest D in order to take account of the fact that the weight of the driver's body generates much larger amplitude variations in the seat base than those generated by this weight in the backrest.

In conclusion, this processing therefore results in determining four thresholds consisting in a mean positive threshold and a mean negative threshold for each of the seat base A and backrest D surfaces.

The last processing operation applied to the signals provided by the pressure sensors takes place once the thresholding phase is completed, and the purpose of this operation is to detect the times at which the values of said signals exceed the threshold values determined during said thresholding phase.

Figure 3:
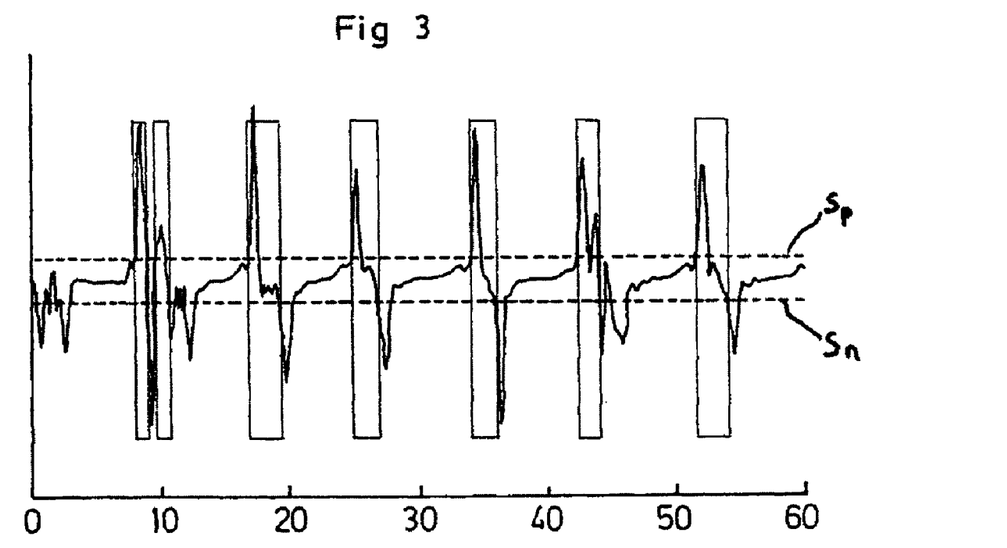
FIGS. 3 and 4 are two graphs illustrating the method according to the invention of processing measurement signals provided by the pressure sensors.
Figure 4:
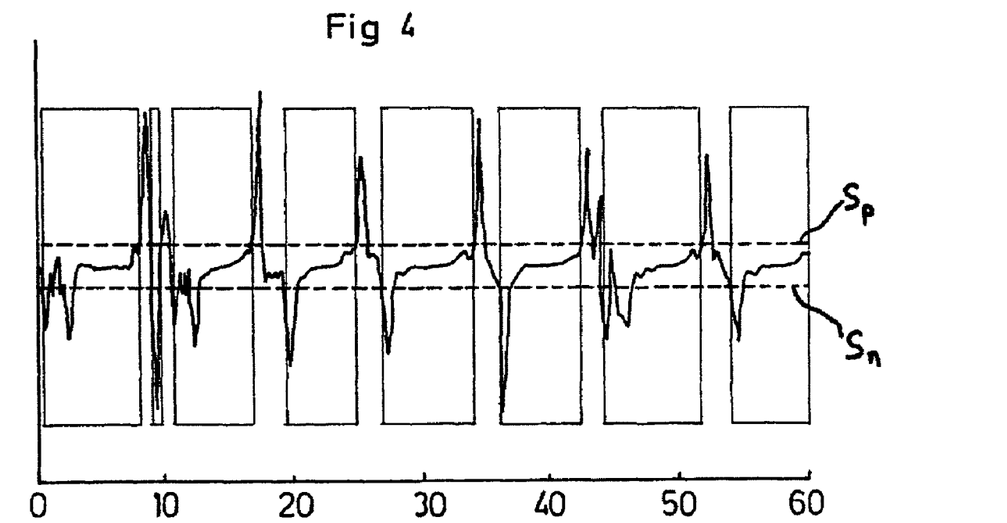

As shown in FIGS. 3 and 4, in which a mean positive threshold Sp and a mean negative threshold Sn are also shown, this processing results in the extraction of:

the sequences, called pressing sequences, shown in FIG. 3, activated by the exceeding of a positive threshold and deactivated by the exceeding of a negative threshold, and which correspond, each of them, to a time period during which the driver is applying a pressure force exerted on the pressure sensor, which ends when this pressure is released, and the sequences, called releasing sequences, shown in FIG. 4, activated by the exceeding of a negative threshold and deactivated by the exceeding of a positive threshold, and which correspond, each of them, to a time period during which the driver "cancels" the pressure force exerted on the pressure sensor, for example due to the absence of contact with said sensor, said period ending at the time of a new pressing applied on the sensor.

The detection method according to the invention furthermore necessitates, in a preliminary phase, the characterizing, essentially by experimental analyses, of specific movements likely to allow the diagnosis of a lowering of vigilance, said characterizing generally consisting:

either in determining one or more geographic zones subjected to a "pressing" or to a "releasing" due to the execution of said movement, or in determining at least one geographic zone subjected to a "pressing" or to a "releasing", as well as a time sequence of stressing said geographic zone consisting in an alternation of a period of activation, by pressing or releasing, and a period of non-activation.

This method furthermore consists in analyzing, at all times, the pressing and releasing zones detected by aggregation of elementary data coming from pressure sensors, and in comparing these detected zones with the predefined characteristic geographic zones.

By way of example, four categories of movements are defined and explained below:

movements of the top of the body: for example, the back detaching from the backrest D, movements toward a driving position offset to one side: for example, a position of leaning against the window or the armrest, movements toward a "pushed-in" driving position in the top of the backrest D: for example, a position of relaxation of the driver when the latter supports himself on the steering wheel, and movements of repositioning on the seat: for example, changing of the zone of pressing on the seat base A or on the backrest D.

(It should be noted that in FIGS. 5 to 8, the geographic zones delimited by full lines correspond to zones whose elementary surfaces must be activated, by a pressing or a releasing, in order to be considered. On the contrary, the geographic zones delimited by dotted lines correspond to zones whose elementary surfaces must not be activated in order to be considered).

Figure 5:
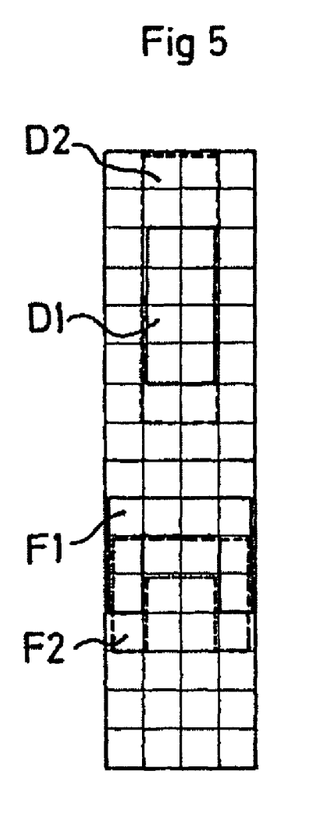
FIG. 5 is a diagrammatic front view of a motor vehicle seat showing a step of the method of detecting a movement of the top of the back.

Firstly, the first movement, relating to a movement of the top of the back, is characterized by four locating geographic zones shown in FIG. 5.

As shown in FIG. 5, two of these geographic zones D1 and D2 are situated on the backrest D and define two surfaces which overlap, centered on the longitudinal axis of symmetry of the backrest D.

The other two zones F1 and F2 are situated on the seat base A and define two surfaces having the same shape and area corresponding to the contact surface between a posterior and said seat base. Moreover, these two zones F1, F2 are offset longitudinally with respect to each other, in such a way however as to have an overlapping portion.

Such a configuration of zones for locating movements of the top of the back allow detection adapted to the various driving postures of an individual.

Moreover, during their activation, the locating zones D1 and D2 consist of releasing zones whereas the other two zones F1 and F2 consist of pressing zones. In fact, the movements of the top of the back are characterized by a detachment of the back with respect to the backrest D, and by an application of a pressing force on the seat base A.

On the basis of these definitions of locating zones, a detected movement is determined as constituting a movement of the top of the back if at least one of the following rules is complied with:

locating zone D1 activated,
locating zone D2 activated,
locating zone F1 activated with a minimal degree of symmetry with respect to a longitudinal axis of the seat base (A), elementary surfaces constituting said locating zone,
locating zone F2 activated with a minimal degree of symmetry with respect to a longitudinal axis of the seat base (A), elementary surfaces constituting said locating zone.

Figure 6A:
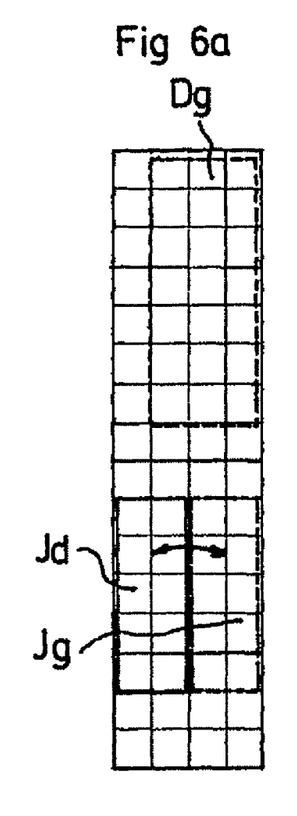
FIGS. 6a and 6b are two diagrammatic front views of a motor vehicle seat illustrating a step of the method of detecting a movement of transition toward a driving position offset to one side.
Figure 6B:
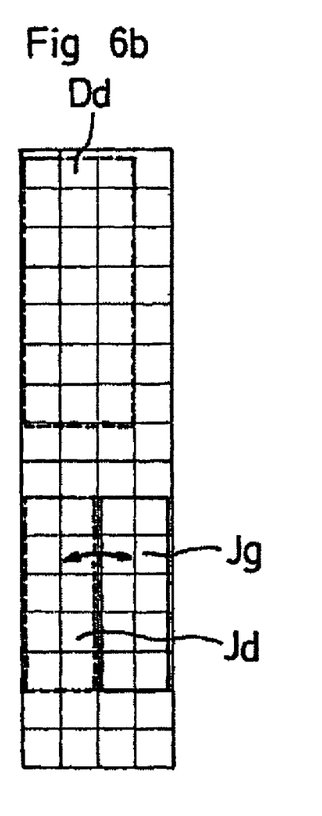

Secondly, the second movement relating to a movement toward a driving position offset to one side is characterized by four geographic locating zones shown in FIGS. 6a and 6b.

Two of these geographic zones Dd, Dg are situated on the backrest D and respectively correspond to contact surfaces between said backrest and the right and left parts of a driver's back.

The other two geographic zones Jd, Jg are situated on the seat base A and respectively correspond to contact surfaces between the left and right legs of the driver and said seat base. Moreover, during their activation, the locating zones Dd and Dg consist of pressing zones whereas the other two zones Jd and Jg consist of releasing zones.

Furthermore, the characterization of this movement also comprises a time component defined by the rules given below, consisting in studying the activation by releasing of a leg and then the activation by releasing of the other leg.

On the basis of this time component and of the definitions of the locating zones, a detected movement is determined as constituting a movement toward a driving position offset to one side if at least one of the following rules is complied with:

locating zone Jg activated, locating zone Jd not activated, whereas this locating zone Jd was previously activated and locating zone Dd not activated.
locating zone Jg not activated, locating zone Jd activated, whereas locating zone Jg was previously activated and locating zone Dg not activated.

Figure 7:
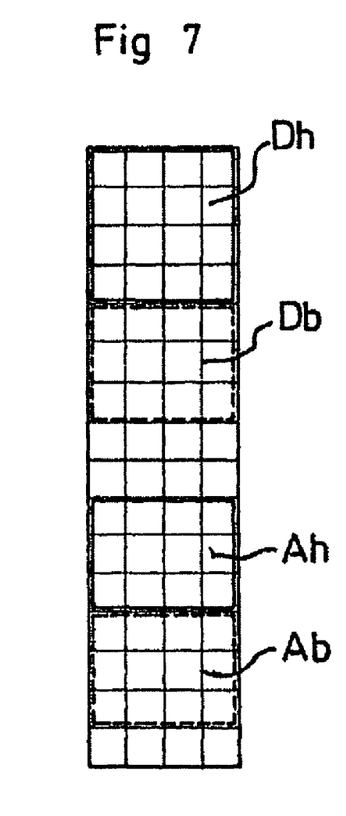
FIG. 7 is a diagrammatic front view of a motor vehicle seat illustrating a step in the method of detecting a movement of transition toward a "pushed-in" driving position in the top of the backrest, and FIGS. 8a-8b, 8c-8d and 8e-8f constitute three groups of figures, each one composed of two diagrammatic front views of a motor vehicle seat illustrating a step of a method of detecting a repositioning movement.

As for the third movement relating to a movement of transition toward a "pushed-in" position in the backrest D, this is characterized by four geographic locating zones shown in FIG. 7.

Two of these geographic zones Dh, Db are situated on the backrest D and respectively correspond to contact surfaces between said backrest and top and bottom parts of a driver's back.

The other two geographic zones Ah and Ab are situated on the seat base A and respectively correspond to contact surfaces between the seat base A and top and bottom parts of the driver's posterior.

Moreover, during their activation, the locating zones Dh and Db consist of pressing zones, whereas the other two zones Ah and Ab consist of releasing zones.

On the basis of these definitions of locating zones, a detected movement is determined as constituting a movement of transition toward a "pushed-in" position in the backrest D if the following rule is complied with:

locating zone Dh activated and locating zone Db not activated, locating zone Ah activated and locating zone Ab not activated.

Finally, three different characterization procedures, shown in FIGS. 8a-8b, 8c-8d and 8e-8f respectively, make it possible to identify a repositioning movement.

For each of these procedures moreover, during their activation, the locating zones situated on the backrest D consist of pressing zones, whilst the locating zones situated on the seat base A consist of releasing zones.

Figure 8A:
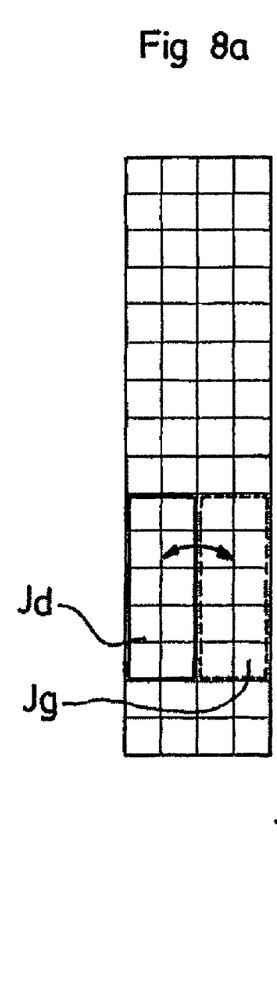
Figure 8B:
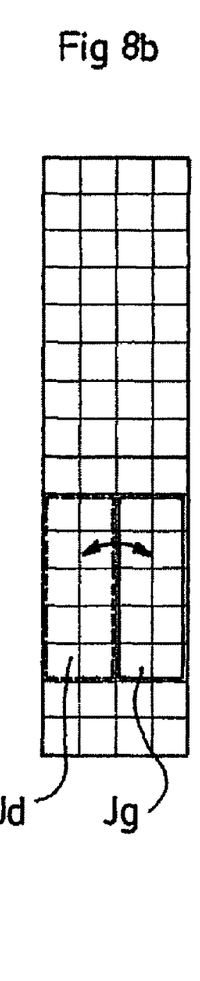

The first procedure is similar to that described with reference to FIGS. 6a and 6b and, according to this procedure, the repositioning movement (of one leg on the other) is characterized by:

two geographic locating zones Jd and Jg, shown in FIGS. 8a and 8b, situated on the seat base A and respectively corresponding to contact surfaces between the left and right legs of the driver and said seat base,
a time component defined by the rules given below, consisting in studying the activation by releasing of one leg and then the activation by releasing of the other leg.

According to this procedure, a detected movement is determined as constituting a repositioning movement if at least one of the following rules is complied with:

locating zone Jg activated, locating zone Jd not activated, whereas this locating zone Jd was previously activated,
locating zone Jg not activated, locating zone Jd activated, whereas locating zone Jg was previously activated.

Figure 8C:
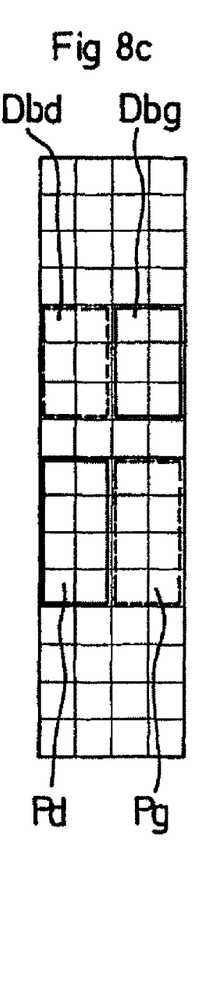
Figure 8D:
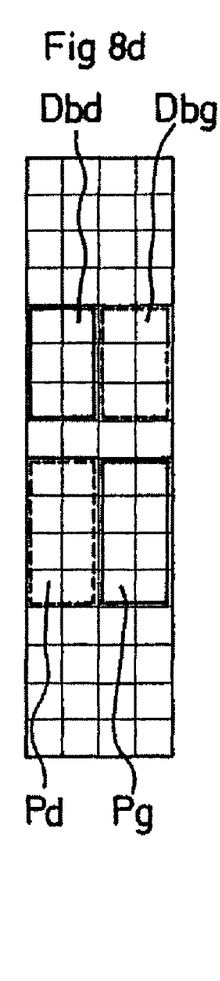

According to the second procedure, a repositioning movement is characterized by four geographic locating zones shown in FIGS. 8c and 8d.

Two of these geographic zones Dbd, Dbg are situated on the backrest D and respectively correspond to contact surfaces between said backrest and the right and left parts of the bottom of a driver's back.

The other two geographic zones Pd, Pg are situated on the seat base A and respectively correspond to contact surfaces between said seat base and the left and right parts of the driver's posterior.

According to this second procedure, a detected movement is determined as constituting a repositioning movement if the following rule is complied with:

locating zone Dbd not activated and locating zone Dbg activated, and locating zone Pd activated and locating zone Pg not activated.

Figure 8E:
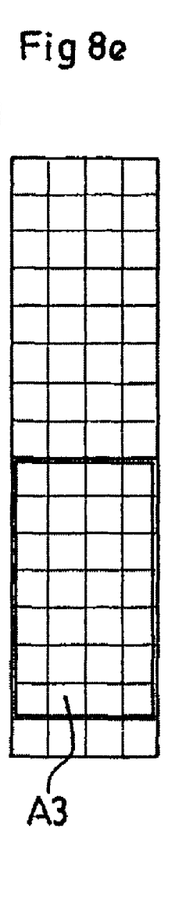
Figure 8F:
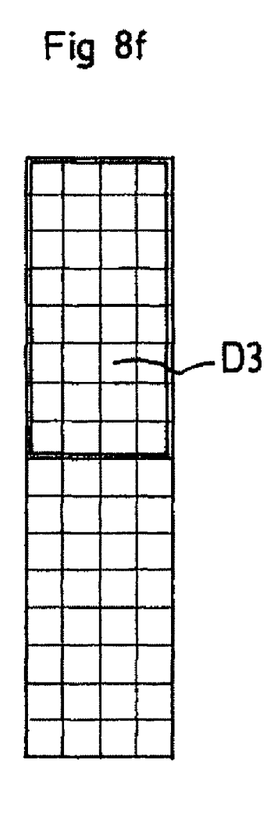

Finally, according to the third procedure, a repositioning movement is characterized by two geographic locating zones consisting in:

a locating zone A3 shown in FIG. 8e, corresponding to a contact surface between the seat base A and the complete posterior of a driver, and a locating zone D3 shown in FIG. 8f, corresponding to a contact surface between the backrest D and the complete back of a driver.

According to this third procedure, a detected movement is determined as constituting a repositioning movement if at least one of the following rules is complied with:

locating zone A3 activated,
locating zone D3 activated.

Moreover, the method according to the invention described above can advantageously make use of fuzzy logic concepts, for example by allocating a weighted weight to each activated elementary surface of a geographic zone, using fuzzy logic rules, depending on:

the geographic position, in particular positioning in a bordering zone, of said elementary surface within the geographic zone,
and/or the amplitude of the signal provided by the associated pressure sensor, representing the level of activation of said elementary surface.

Moreover, in this case, for each geographic zone the following is determined a degree of activation of the latter calculated from the weight of each of its elementary surfaces, in order to associate with each item of information of detection of a specific movement, information representing the degree of belonging to this movement category.

Finally, a final consistency analysis makes it possible to provide more robust results. This consistency analysis consists in carrying out, whilst the data processing is in progress, an on-line appraisal of the results coming from the classification of the specific movements.

More specifically, such a consistency analysis consists, in terms of sliding processing windows of a given conventional duration, on the one hand of eliminating isolated data (artifacts) and on the other hand aggregating disconnected sequences relating to an identical item of data.

The invention claimed is:

1. A method for detecting characteristic movements of a vehicle driver in the driving position on a seat (S) comprising a seat base (A) and a backrest (D), for the purpose of diagnosing a lowering of vigilance by said driver, said detection method comprising:

dividing the surface of the seat base (A) and of the backrest (D) of the seat (S) into a plurality of elementary surfaces in each of which is embedded a pressure sensor (An,n-Dn,n) able to detect:
an increase in the pressure applied on the elementary surface, representing a positive pressure, called "pressing" applied by the driver on the pressure sensor,
a reduction of the pressure applied on the elementary surface, representing a reduction or a cancellation, called "releasing", of the pressure applied by the driver on the pressure sensor,
selecting a plurality of specific movements, comprising the movements of the top of the body, repositioning on the seat base (A), transverse rocking toward a driving position offset to one side, longitudinal rocking toward a pushed-in driving position in the top of the backrest (D), and characterizing each of said specific movements by the determination of at least one geographic zone subjected to a "pressing" or a "releasing" resulting from said movement,
and analyzing, with a given sampling period, the measurement signals provided by the pressure sensors (An,n-Dn,n), and comparing, at each sampling time t, the possible geographic zones of pressing or releasing detected with each of the predetermined geographic zones, in such a way as to provide information on detecting a specific movement during a correlation between said geographic zones, said specific movements corresponding to zones enveloping contact surfaces of various parts of the driver's body with the seat base (A) and the backrest (D): complete back, parts of the back (left, right, top, bottom), complete posterior or bottom or top part of the posterior, posterior or parts of posterior (right or left), left or right leg, etc., wherein said method consists, for the purpose of characterization of given specific movements, in determining at least one geographic zone subjected to a "pressing" or a "releasing", and a time sequence of stressing said geographic zone comprising of an alternation of a period of activation, by pressing or releasing, and a period of non-activation.

2. The method as claimed in claim 1 for detecting a movement of the top of the back, wherein:

for the purpose of characterizing said movement, the following are determined:
at least one geographic zone (D1, D2) subjected to a "pressing", corresponding to a zone enveloping contact surfaces between the central portion of a driver's back and the backrest (D)
and at least one geographic zone (F1, F2) subjected to a "releasing", corresponding to a zone enveloping contact surfaces between a driver's posterior and the seat base (A),
and information on the detection of a movement of the top of the back is provided uniquely when there is correlation of a detected geographic zone with:
a said geographic zone (D1, D2) of the backrest (D),
and/or a said geographic zone (F1, F2) of the seat base (A), provided that there is, in addition, a minimal degree of symmetry, with respect to a longitudinal axis of the seat base (A), of the elementary surfaces constituting said detected geographic zone.

3. The method as claimed in claim 1 for detecting a repositioning movement, wherein:

for the purpose of the characterization of said movement, two geographic zones (Jd, Jg) subjected to a "releasing" are determined, each one corresponding with a zone enveloping the contact surface between a leg of the driver and the seat base (A),
and information on the detection of a repositioning movement is provided uniquely at the time of detection of the following time sequence:
at a time t: correlation of a detected geographic zone with one of said geographic zones (Jd, Jg) of the seat base (A),
and at a time t+1: absence of activation of the correlated geographic zone (Jd, Jg) at time t, combined with a correlation of a detected geographic zone with the other geographic zone (Jg, Jd) of the seat base (A).

4. The method as claimed in claim 1 for detecting a repositioning movement, wherein:

for the purpose of characterizing said movement, the following are determined:
two geographic zones (Dbd, Dbg) subjected to a "pressing", corresponding to the two respective zones enveloping contact surfaces between the right and left parts of the bottom of a driver's back and the backrest (D),
and two geographic zones (Pd, Pg) subjected to a "releasing", corresponding with the two respective zones enveloping contact surfaces between the left and right parts of a driver's posterior and the seat base (A), and information on the detection of a repositioning movement is provided when there is, simultaneously:
correlation of a detected geographic zone with a said right (or left) geographic zone (Dbd, Dbg) of the backrest (D), combined with the absence of activation of the other said geographic zone (Dbg, Dbd) of the backrest (D),
correlation of a detected geographic zone with said left (or right) geographic zone (Pg, Pd) of the seat base (A), combined with the absence of activation of the other said geographic zone (Pd, Pg) of the seat base (A).

5. The method as claimed in claim 1 for detecting a repositioning movement, wherein:
for the purpose of characterizing said movement, the following are determined:
a geographic zone (D3) subjected to a "pressing", corresponding to the zone enveloping the contact surface between the complete back of a driver and the backrest (D),
and a geographic zone (A3) subjected to a "releasing", corresponding to the zone enveloping the contact surface between the complete posterior of a driver and the seat base (A),
and information on the detection of a repositioning movement is provided when there is correlation between a detected geographic zone and said geographic zone (D3) of the backrest (D) and/or said geographic zone (A3) of the seat base (A).

6. The method as claimed in claim 1 for detecting a movement of transition toward an offset driving position, wherein:
for the purpose of characterizing said movement, the following are determined:
two geographic zones (Dd, Dg) subjected to a "pressing", corresponding to two respective zones enveloping contact surfaces between the right and left parts of a driver's back and the backrest (D),
and two geographic zones (Jd, Jg) subjected to a "releasing" each corresponding to a zone enveloping the contact surface between a leg of the driver and the seat base (A),
and information on the detection of a transition movement is provided uniquely at the time of detection of the following time sequence:
at a time t: correlation of a detected geographic zone with one of said geographic zones (Jd, Jg) of the seat base (A), and absence of activation of the geographic zone (Dg, Dd) of the backrest (D) symmetrical with said detected zone of the seat base (A),
at a time t+1: absence of activation of the correlated geographic zone (Jd, Jg) of the seat base (A) at time t, combined with a correlation of a detected geographic zone with the other geographic zone (Jg, Jd) of the seat base (A).

7. The method as claimed in claim 1 for detecting a movement of transition toward a "pushed-in" driving position in the top of the backrest (D), wherein:
for the purpose of characterizing said movement, the following are determined:
two geographic zones (Dh, Db) subjected to a "pressing", corresponding to two respective zones enveloping contact surfaces between the top and bottom parts of a driver's back and the backrest (D),
and two geographic zones (Ah, Ab) subjected to a "releasing", corresponding with two respective zones enveloping contact surfaces between the top and bottom parts of a driver's posterior with the seat base (A),
and information on the detection of a transition movement is provided at the time, on the one hand, of simultaneous correlation of two detected geographic zones with, respectively, said geographic zones (Dh, Ah) corresponding to the top parts of the back and of the posterior and, on the other hand, the combined absence of activation of said geographic zones (Db, Ab) corresponding with the bottom parts of the back and of the posterior.

8. The detection method as claimed in claim 1, wherein the pressure sensors (An,n-Dn,n) consist of differential pressure sensors able to measure the dynamics of the force applied to the corresponding elementary surface.

9. The detection method as claimed in claim 8, wherein, during a preliminary phase following the starting of the vehicle, called a thresholding phase, there is carried out a processing of the signals provided by the pressure sensors (An,n-Dn,n), comprising in calculating, for each of said sensors, the respective means of the largest positive and negative variations of the values of said signals, in order to determine respectively negative and positive threshold values for the subsequent extraction of signals.

10. The detection method as claimed in claim 1, wherein:
each activated elementary surface of a geographic zone is allocated a weight weighted by the use of a mathematical method comprising fuzzy logic, as a function of:
the geographic position, in particular positioning in a bordering zone, of said elementary surface within the geographic zone,
and/or the amplitude of the signal provided by the associated pressure sensor, representative of the level of activation of said elementary surface,
and, for each geographic zone, the following is determined a degree of activation of the latter calculated from the weight of each of the elementary surfaces, in such a way as to associate with each item of information of detection of a specific movement, information representing the degree of belonging to this category of movement.

* * * * *